United States Patent [19]
Ghirardi et al.

[11] Patent Number: 5,871,952
[45] Date of Patent: Feb. 16, 1999

[54] PROCESS FOR SELECTION OF OXYGEN-TOLERANT ALGAL MUTANTS THAT PRODUCE $H_2$ UNDER AEROBIC CONDITIONS

[75] Inventors: Maria L. Ghirardi; Michael Seibert, both of Lakewood, Colo.

[73] Assignee: Midwest Research Institute, Kansas City, Mo.

[21] Appl. No.: 835,897

[22] Filed: Apr. 14, 1997

[51] Int. Cl.⁶ ............................ C12Q 1/04; C12N 1/12
[52] U.S. Cl. .................. 435/34; 435/168; 435/173.1; 435/173.9; 435/244; 435/245; 435/257.1; 435/257.6
[58] Field of Search ................. 435/168, 257.1, 435/257.6, 244, 245, 173.1, 173.9, 34

[56] References Cited

U.S. PATENT DOCUMENTS

| | | | |
|---|---|---|---|
| 3,320,693 | 5/1967 | Shirota et al. | 435/168 |
| 4,442,211 | 4/1984 | Greenbaum | 435/168 |
| 4,532,210 | 7/1985 | Miura et al. | 435/168 |
| 4,774,186 | 9/1988 | Schaefer, Jr. et al. | 435/257 |
| 4,777,135 | 10/1988 | Husted et al. | 435/160 |
| 5,100,781 | 3/1992 | Greenbaum | 435/34 |

OTHER PUBLICATIONS

McBride, A.C., Lien, S., Togasaki, R.K. and San Pietro, A. (1977), in Biological Solar Energy Conversion (A. Mitsui, S. Miyachi, A. San Pietro, and S. Tamura, eds.) Academic Press, New York.

Harris, E.H. (1989), The Chlamydomonas Sourcebook, Academic Press, New York.

Vladimirova, M.G., and Markelova, A.G. (1980), Sov. Plant Physiol. 27, 878–889.

Happe, T. Mosler, B., Naber, J.D. (1994), Eur J. Biochem. 222, 769–774.

Roessler, P., and Lien, S. (1982), Arch. Biochem. Biophys. 213, 37–44.

McTavish, H., Picorel, R., and Siebert, M. (1989), Plant Physiol. 89, 452–456.

Roessler, P.G., and Lien, S. (1984), Plant Physiol. 76, 1086–1089.

Asada K. (1984), Methods in Enzymology vol. 105, pp. 422–429, Academic Press, New York.

Schmidt, G.W., Matlin, K.S., and Chua, N.–H. (1977) Proc. Natl. Acad. Sci. USA 74, 610–614.

Kindle, K.L. (1990) Proc Natl Acad Sci USA 87, 1228–1232.

*Primary Examiner*—Herbert J. Lilling
*Attorney, Agent, or Firm*—Ken Richardson

[57] ABSTRACT

A process for selection of oxygen-tolerant, $H_2$-producing algal mutant cells comprising:
(a) growing algal cells photoautotrophically under fluorescent light to mid log phase;
(b) inducing algal cells grown photoautrophically under fluorescent light to mid log phase in step (a) anaerobically by (1) resuspending the cells in a buffer solution and making said suspension anaerobic with an inert gas; (2) incubating the suspension in the absence of light at ambient temperature;
(c) treating the cells from step (b) with metronidazole, sodium azide, and added oxygen to controlled concentrations in the presence of white light.
(d) washing off metronidazole and sodium azide to obtain final cell suspension;
(e) plating said final cell suspension on a minimal medium and incubating in light at a temperature sufficient to enable colonies to appear;
(f) counting the number of colonies to determine the percent of mutant survivors; and
(g) testing survivors to identify oxygen-tolerant $H_2$-producing mutants.

10 Claims, 5 Drawing Sheets

PROCESS FOR SELECTION OF OXYGEN-TOLERANT ALGAL MUTANTS THAT PRODUCE $H_2$ UNDER AEROBIC CONDITIONS

CONTRACTUAL ORIGIN OF THE INVENTION

The United States Government has rights in this invention under Contract No. DE-AC36-83CH10093 between the United States Department of Energy and the National Renewable Energy Laboratory, a division of Midwest Research Institute.

FIELD OF THE INVENTION

The invention relates to a process for selecting oxygen-tolerant algal mutants that produce hydrogen under aerobic conditions, based on the toxic effect of metronidazole (MNZ) on photosynthetic organisms.

BACKROUND OF THE INVENTION

There are three major classes of organisms that photo-produce $H_2$: photosynthetic bacteria; cyanobacteria; and green algae.

Photosynthetic bacteria utilize reductants other than water to produce $H_2$, in a reaction catalyzed by the enzyme nitrogenase. While this reaction is energy intensive, requiring at least 4 ATP (Adenosine Triphosphate)/$H_2$ produced, it is also quite functional when waste reductant is available.

Cyanobacteria also produce $H_2$ via a nitrogenase enzyme system and in some cases, such as with the genus Spirilina, via a hydrogenase system. In the case of the nitrogenase system, the source of reductant is $H_2O$, but the reaction can involve the formation of a metabolic intermediate. As a result, the quantum yield of $H_2$ production is rather low, in the order of 1 $H_2$/9–10 quanta.

Algae do not synthesize nitrogenase; rather, $H_2$ production in these organisms is catalyzed by the hydrogenase enzyme. Algal $H_2$ production does not require ATP input nor the generation of metabolic intermediates. Consequently, a higher theoretical quantum yield of 1$H_2$/4 quanta is possible.

The desired characteristics of a photobiological $H_2$-production system are:
a) The use of water as the source of reductant;
b) solar-driven;
c) high efficiency of solar energy conversion;
d) durable and self-replicating;
e) $H_2$ production at high equilibrium pressure; and
f) cost-competitiveness.

On the basis of these criteria, the use of algae such as green algae should be promising and attractive for photobiological $H_2$-production—however, the current practical limitations of green algae in a photobiological $H_2$—evolving system include:

(1) The sensitivity of its hydrogenase to $O_2$; (2) the occurence of a dark back reaction between $O_2$ and $H_2$ (i.e., the oxy-hydrogen reaction); (3) competition between the $CO_2$-fixation and the $H_2$-production pathways for electrons from $H_2O$, (4) the low equilibrium pressure of $H_2$ release; and (5) saturation of $H_2$ production capacity at low light intensity.

A biological approach to address the hydrogenase $O_2$-sensitivity draw back in green algae was developed approximately 20 years ago by McBride et al. [1]. This approach used a positive selection technique based on the reversible $H_2$ uptake reaction catalyzed by algal hydrogenases. Mutants were selected under this photoreductive pressure and increasing concentrations of $O_2$. These conditions require algal cells to utilize $H_2$ as a source of reducing equivalents to fix $CO_2$ in the presence of DCMU,3-(3,4-dichlorophenyl)-1,1-dimethyl urea, an inhibitor of electron flow from water. As a consequence, cells with hydrogenase sensitive to low oxygen concentration die, while cells with an $O_2$-tolerant hydrogenase grow. Oxygen-tolerant mutants of Chlamydomonas reinhardthii obtained by this technique could produce $H_2$ in the presence of up to 8% $O_2$. Unfortunately, the mutants exhibited high levels of oxy-hydrogen back reactions and were not maintained in culture, and thus could not be utilized for further study.

[1] McBride, A. C., Lien, S., Togasaki, R. K., and San Pietro, A. (1977), in Biological Solar Energy Conversion (A. Mitsui, S. Miyachi, A. San Pietro, and S. Tamura, eds.) Academic Press, New York.

One prior art group of patents, namely, U.S. Pat. No. 3,320,693; U.S. Pat. No. 4,774,186; and U.S. Pat. No. 4,777,135 disclose, respectively: cultivation of Chlorella green algae selected to grow without light; an algal cover crop of Chlamydomonas and other species; and the production of butanol by fermentation. The organism is grown in the presence of a fluorocarbon, thereby making the fermentation process more efficient. However, the foregoing U.S. Patents deal with commercial uses of algae, other than as associated with the production of $H_2$.

On the other hand, U.S. Pat. Nos. 4,532,210; 4,442,211; and 5,100,781; disclose, respectively: an algal process for producing hydrogen and the cultivation of Chlamydomonas reinhardtii; hydrogen and oxygen generation using Chlamydomonas reinhartii; and methods for the screening of algal colonies for gas production. In other words, the '210 and '211 patents describe processes to deal with the oxygen sensitivity of algal hydrogen production, either by temporarily separating $O_2$ evolution (light cycle) from $H_2$ evolution (dark cycle), or by developing a system that is constantly being purged with an inert gas to remove simultaneously produced $O_2$ and $H_2$ (as per the '211 patent); and, the '781 patent describes a technique to measure $H_2$ evolution by individual immobilized algal colonies in the absence of $O_2$.

None of the patents describe processes that attempt to generate and select for organisms or strains that evolve $H_2$ in the presence of $O_2$ —albeit their existence appears to underline the extreme importance of oxygen in deactivation of the hydrogen-producing enzyme.

SUMMARY OF THE INVENTION

One object of the present invention is to provide algal hydrogenases and/or associated metabolic processes or pathways that are stable in the presence of $O_2$.

Another object of the invention is to provide a process for obtaining algal hydrogenases and/or associated metabolic processes or pathways that are stable in the presence of $O_2$ by the application of selective pressure under $H_2$-producing, rather than $H_2$-utilizing conditions.

A yet further object of the invention is to obtain algal hydrogenases and/or associated metabolic processes or pathways that are stable in the presence of $O_2$ and eliminate the high rates of oxy-hydrogen reaction attendant to prior reactions.

The foregoing and other objects of the invention are accomplished by utilizing the toxic effect of metronidazole (MNZ) on photosynthetic organisms in which hydrogenase and MNZ compete for electrons through Fd. In these organisms, MNZ is a strong oxidizer of ferredoxin (Fd), in a reaction that competes with electron transport to the reversible hydrogenase in the absence of carbon dioxide. The site of action of MNZ in photosynthetic organisms is restricted to chloroplasts, where it oxidizes light-reduced ferredoxin.

BRIEF DESCRIPTION OF THE DRAWINGS

In A, selection was done using cw15 cells (a cell wall-less strain of Chlamydomonas reinhardtii) in the presence of varying concentrations of MNZ and 2.8% $O_2$, at either 17.5 or 50 W/m$^2$. In B, the selection was done as in A, but under either 200 or 400 W/m$^2$.

FIG. 2 shows the effect of anaerobic pre-induction of hydrogenase on the number of cw15 survivors. Cells submitted to the MNZ selective treatment were either pre-induced by anaerobic incubation or not induced, as described in the Materials and Methods section hereafter described. The treatment was done in the presence of 2.8% $O_2$ and 200 W/m$^2$ light intensity.

FIG. 5 shows initial rates of $H_2$ evolution measured in the presence of different initial concentrations of $O_2$ in the assay medium. Open circles represent data taken with the control cw15 strain of Chlamydomonas reinhartii. Closed circles represent data taken with the D5 variant, which was obtained from application of selective pressure to cw15 cells in the presence of 2.8% $O_2$. Asterisks represent results obtained with the IM6 mutant, a survivor from the application of selective pressure to the mutagenized variant D5 in the presence of 5% $O_2$. All data were normalized to $V_o$=76 $\mu$moles $H_2 \times$mg Chl$^{-1} \times$h$^{-1}$.

DESCRIPTION OF THE PREFERRED EMBODIMENTS

EXAMPLE 1
MATERIALS AND METHODS
Cell Growth

Wild-type (WT) Chlamydomonas reinhardtii (137 mt$^+$) was obtained locally, and a cell wall-less strain, cw15(cc400 mt$^+$), was acquired at the Chlamydomonas Genetics Center, Duke University. Wild-type cells were grown photoautotrophically in Sager's minimal medium [2]. The cw15 strain required Sueoka's high salt medium modified according to Vladimivora & Markelova [3]. Both cultures were grown in a chamber at 25° C. under 8 W/m$^2$ fluorescent cool white illumination and continous bubbling with a mixture of 1.7% $CO_2$ and air. Cells were harvested by centrifugation at 1000 x g for ten minutes. Wild-type and cw 15 cells were also grown on plates containing 1.5% and 0.8% agar, respectively.

[2] Harris, E. H. (1989), The Chlamydomonas Sourcebook, Academic Press, New York.
[3] Vladimirova, M. G., and Markelova, A. G. (1980), Sov. Plant Physiol. 27, 878–889.

EXAMPLE 2
ANAEROBIC INDUCTION OF CELLS

Harvested cells were resuspended in a small volume of buffer (50 mM potassium phosphate buffer, pH 7.2, containing 3 mM $MgCl_2$ [4]) at a final concentration of about 200 $\mu$g Chl·ml$^{-1}$. [5] In order induce the hydrogenase enzyme, the cell suspension was made anaerobic by bubbling argon for 30 minutes. Maintenance of anaerobic condition was insured by the addition of a glucose/catalase/glucose oxidase oxygen scrubbing system ([6]). Chlamydomonas reinhardtii cells cannot use glucose as a carbon source for growth. The mixture was incubated at room temperature for four hours in the dark ([7]). For convenience, it was transferred to 4° C. for overnight storage until assayed the next morning.

[4] Happe, T. Mosler, B., Naber, J. D. (1994), Eur. J. Biochem. 222, 769–774.
[5] Roessler, P., and Lien, S. (1982), Arch. Biochem. Biophys. 213, 37–44.
[6] McTavish, H., Picorel, R., and Seibert, M. (1989), Plant Physiol. 89, 452–456.
[7] Roessler, P. G., and Lien, S. (1984), Plant Physiol. 76, 1086–1089.

EXAMPLE 3
$H_2$ PRODUCTION SELECTION TECHNIQUE

For $H_2$-production selection, anaerobically-treated cells (without addition of an $O_2$ scrubbing system) were added to a selective medium containing different concentrations of metronidazole and 1 mM sodium azide ([8]). The azide inhibits endogenous catalase activity. All procedures were done under sterile conditions. The selection medium was also made anaerobic by argon bubbling before introduction of the cells. Oxygen was then added to the medium to achieve final concentrations of $O_2$ in the gas phase ranging from 0–10% or higher, as required. The final cell suspension was exposed to light of controlled intensity (Fiber-Lite High Intensity Illuminator, model 170-D Dolan-Jenner Industries, Inc.) for 20 minutes. The cells were pelleted out using a clinical centrifuge, washed once with phosphate buffer, pH 7.0, and then once with resuspension buffer (5 mM potassium phosphate buffer containing 1 mM $CaCl_2$ and 1 mM $Mg_2SO_4$). Undiluted and sequential dilutions of each sample were plated on minimal medium and incubated in a growth chamber under low light levels. Survival rates were determined by counting the number of colonies detected on each plate following the treatment, and estimating the percentage of survivors with respect to the number of cells at the beginning of the MNZ treatment.

[8] Asada K. (1984), Methods in Enzymology vol. 105, pp. 422–429, Academic Press, New York.

EXAMPLE 4
$H_2$ EVOLUTION MEASUREMENTS

Anaerobically-treated cells were added to a small volume of the assay buffer (50 mM MOPS, pH 6.8) ([5]) to a final concentration of about 15 $\mu$g Chl/ml. The medium, placed in the assay chamber of a 2-electrode apparatus (Clark-type, YSI 5331) ([5]), was adjusted to different initial concentrations of $O_2$ before introduction of the cells. $H_2$ evolution was induced by illumination with saturating light from the same Illuminator described above, except that a heat filter consisting of 1% solution of $CuSO_4$ was used. The data were recorded on a strip-chart recorder and initial rates of the evolution were calculated from the initial slopes of each curve. Initial $O_2$ concentrations were also determined from the recorded $O_2$ concentration measured at the time when the cells were introduced into the chamber. Gas concentrations were corrected for their decreased solubility in aqueous solution at 1,580 m above sea level.

[5] Roessler, P., and Lien, S. (1982), Arch. Biochem. Biophys. 213, 37–44.

RESULTS

The hydrogen-production selective pressure employed in this invention is based on the toxic effect of metronidazole (MNZ) on photosynthetic organisms.

Metronidazole is a heterocyclic compound with a low redox potential ($E_m = -325$ mV at pH 6.9) that is normally used to treat infections caused by protozoa and anaerobic bacteria. In these organisms, MNZ is a strong oxidizer of ferredoxin, in a reaction catalyzed by the reversible hydrogenase. Its toxic effect is due to one of its reduced intermediate states. The site of the MNZ action in photosynthetic organisms is restricted to chloroplast, where it oxidizes light-reduced ferredoxin. Schmidt et al. ([10]) have proposed that the subsequent reoxidation of reduced MNZ by molecular $O_2$ yields a superoxide radical which then disproportionates into $H_2O_2$. Consequently, the toxicity of MNZ is attributed to the generation of $H_2O_2$. Long exposure (up to 24 hours) to MNZ is used to select for Chlamydomonas mutants defective in photosynthetic electron transport function.

[10] Schmidt, G. W., Matlin, K. S., and Chua, N.-H. (1977) *Proc. Natl. Acad. Sci. USA* 74, 610–614.

Ferredoxin (Fd) is a key electron carrier, located on the reducing side of photosystem I, and it provides the reducing equivalents to a variety of pathways. The most prevalent pathway is through NADP (nicotinamide adenine dinucleotide phosphate) which in turn is coupled to $CO_2$ fixation. Among the other Fd-dependent pathways is hydrogenase-catalyzed $H_2$ production. This pathway is inoperative during phototrophic growth due to inactivation of the enzyme by $O_2$ produced during the water-splitting process. Since MNZ toxicity depends on the accumulation of reduced Fd, an organism with an active hydrogenase will be less sensitive to MNZ toxicity in the absence of $CO_2$ because an alternative pathway for electrons from Fd is available.

On the basis of the above information, a treatment was designed to select for potential $O_2$-tolerant, $H_2$-producing organisms. Cells were first incubated in the presence of MNZ at different concentrations of $O_2$ for a short period of time in the light, next the MNZ was washed out by centrifugation, and then cells were grown on minimal agar medium to determine survival rates.

The effect of the following treatment parameters on the rate of survival was examined: MNZ concentration, light intensity (which limits the rate of accumulation of reduced Fd required for reduction of MNZ), pre-induction of the hydrogenase enzyme, and $O_2$ concentration in the selection medium. Both WT (wild-type) and a cell wall-less strain (cw15) of *Chlamydomonas reinhardtii*, were tested, to determine if a mutant containing an $O_2$-tolerant hydrogenase was isolated. The choice of the cw15 strain was based on the observation that the absence of the cell wall increases the efficiency of genetic transformation ([11]) which may prove valuable for future work.

[11] Kindle, K. L. (1990) *Proc Natl Acad Sci* USA 87, 1228–1232.

Figure 1:
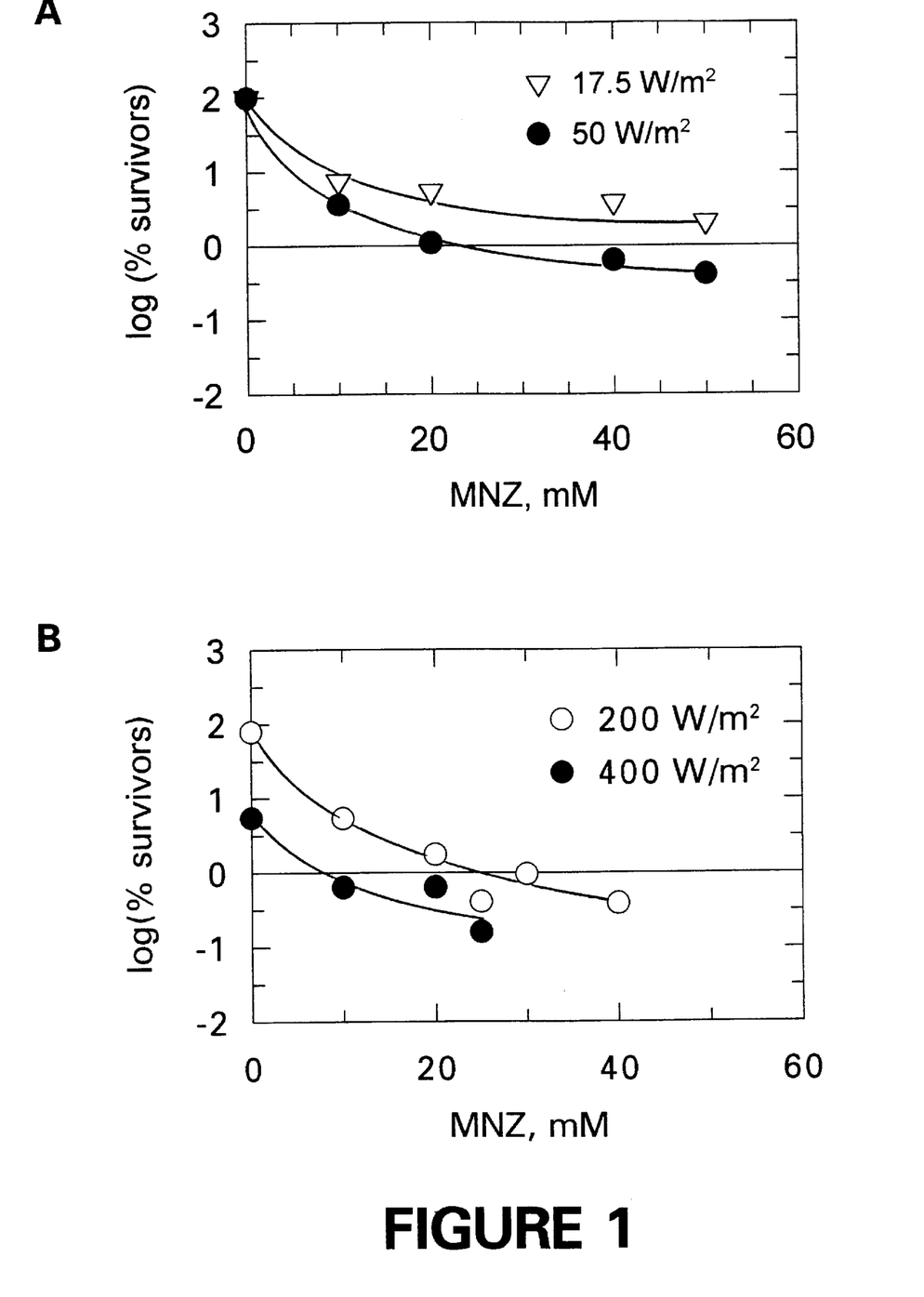
FIGS. 1A and 1B depicts the effect of MNZ concentration and light intensity on the number of survivors from two selected experiments.

FIG. 1 shows the effect of increasing concentrations of MNZ and light intensity on the number of cw15 Chlamydomonas cells surviving the selective treatment. The light intensities were 17.5, 50 (FIG. 1A, first experiment), 200, and 400 (FIG. 1B, second experiment) W/m². The selective pressure was applied to anaerobically-treated cells (containing an initially active hydrogenase), and $O_2$ was added at 2.8 percent. Oxygen inhibits most of the hydrogenase activity in both WT and cw15 cells at this concentration (see FIG. 4). The maximum concentration of MNZ used in the treatment (58 mM) was determined by the solubility of MNZ in aqueous medium (about 60 mM).

It is clear from FIG. 1 that MNZ toxicity is a function of the light intensity, consistent with the theory that the extent of killing depends on the rate of the electron transport. The curves in FIG. 1 do not fit an exponential function, which suggests that factors other than MNZ concentration are limiting the rate of killing (see the hydrogenase induction experiment below). FIG. 1 also shows the degree of variability of the results obtained from different experiments. The data obtained by exposure of cells to 50 W/m² in the first experiment (FIG. 1A) is very similar to the data obtained with 200 W/m² in the second experiment FIG. 1(B). Without wishing to be bound by any theory, it is believed that the phase of growth in which cells were harvested for each experiment is responsible for the variability. Alternatively, variability in setting the initial oxygen concentration during MNZ treatment could cause some variability of the results.

On the other hand, treatment done in the presence of light intensities above 200 W/m² (FIG. 1B) caused an increase in temperature that may have affected the number of survivors detected even in control samples not exposed to MNZ.

Figure 2:
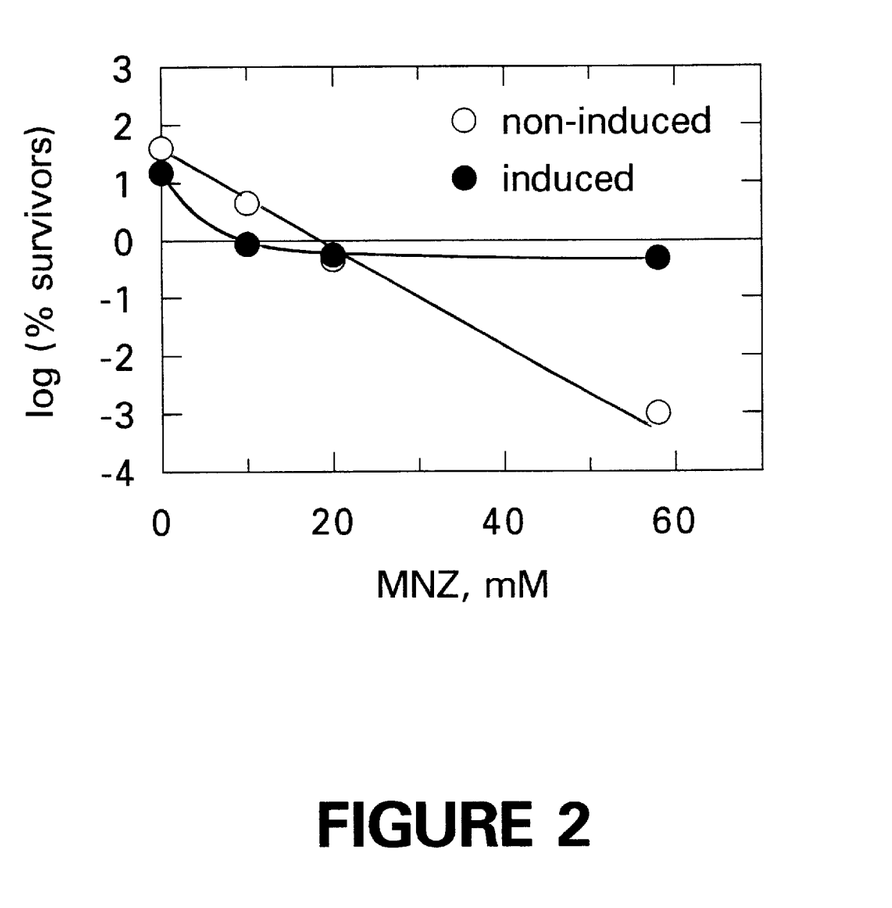

The third parameter checked was the effect of hydrogenase induction on the number of survivors. The experiment was done with pre-induced and uninduced cw15 Chlamydomonas cells subsequently treated with different concentrations of MNZ in the presence of 2.8 percent $O_2$ and illuminated for 20 minutes at 200 W/m². FIG. 2 shows that the MNZ killing in the absence of the pre-induced hydrogenase is exponential. However, pre-induction of the hydrogenase causes a loss of exponential killing, consistent with the results in FIG. 1. This demonstrates that the effect of MNZ is limited in cells that have an active hydrogenase, and confirms the belief that hydrogenase-catalyzed $H_2$-production provides enough of an alternative sink for electrons from reduced Fd to mitigate the effects of MNZ.

We have found that our selection technique depends on the concentration of MNZ, on the amount of accumulated reduced Fd (and thus on the electron transport rate), and on the presence of an active hydrogenase.

Figure 3:
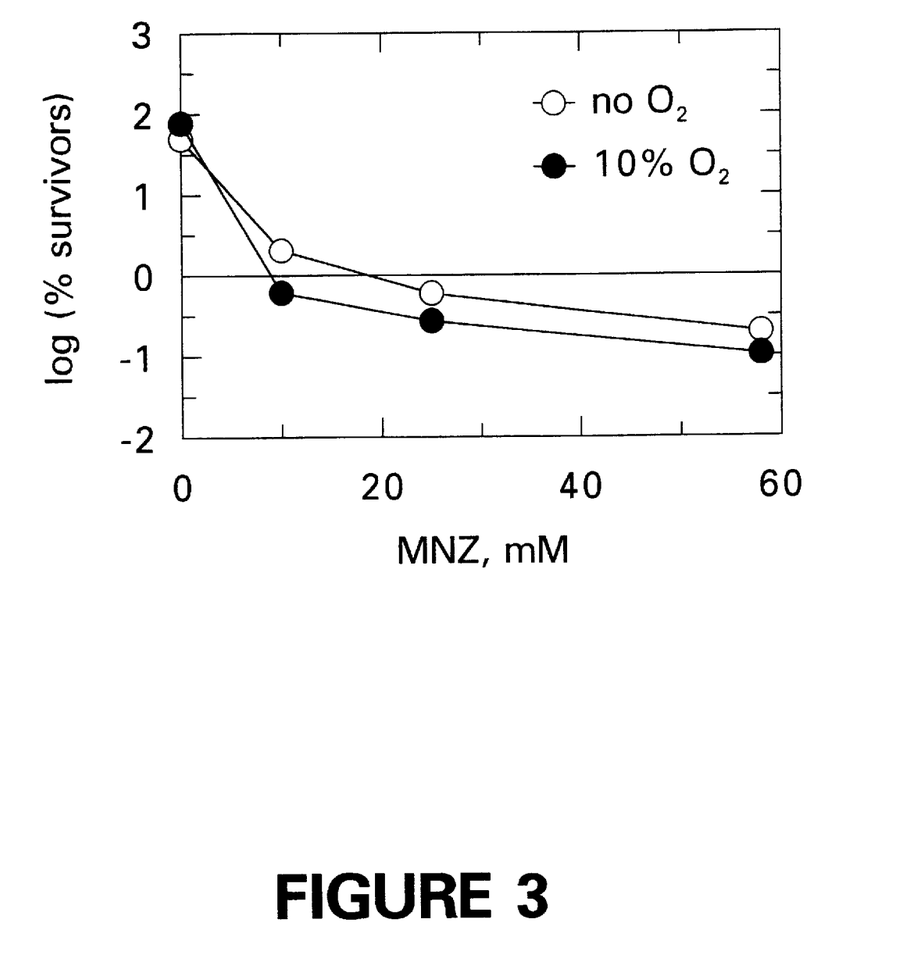
FIG. 3 demonstrates the effect of $O_2$ concentration in the gas phase of the selective treatment vial on the number of survivors. MNZ incubation was done using cw15 cells, either under completely anaerobic conditions, or in the presence of 10% added $O_2$ in the gas phase of the selection medium. The light intensity was 200 W/m$^2$.

Next, the effect of the $O_2$ concentration on the rate of survival was examined. Oxygen is expected to inactivate the hydrogenase in a concentration-dependent manner, thus increasing the toxicity of MNZ. FIG. 3 shows the result of adding 10% of $O_2$ to the gas phase of the selection medium on the degree of survival of cw15 Chlamydomonas cells treated with MNZ and exposed to 200 W/m² light. While the increase in $O_2$ concentration in gas phase appears to increase the sensitivity of MNZ-dependent killing, the magnitude of the increase is not as pronounced as would be expected. One possibility is that internally generated photosynthetic $O_2$ production from the light driven, water-splitting process is affecting the MNZ treatment in part, and the impact of externally-set $O_2$ is superimposed on it.

Figure 4:
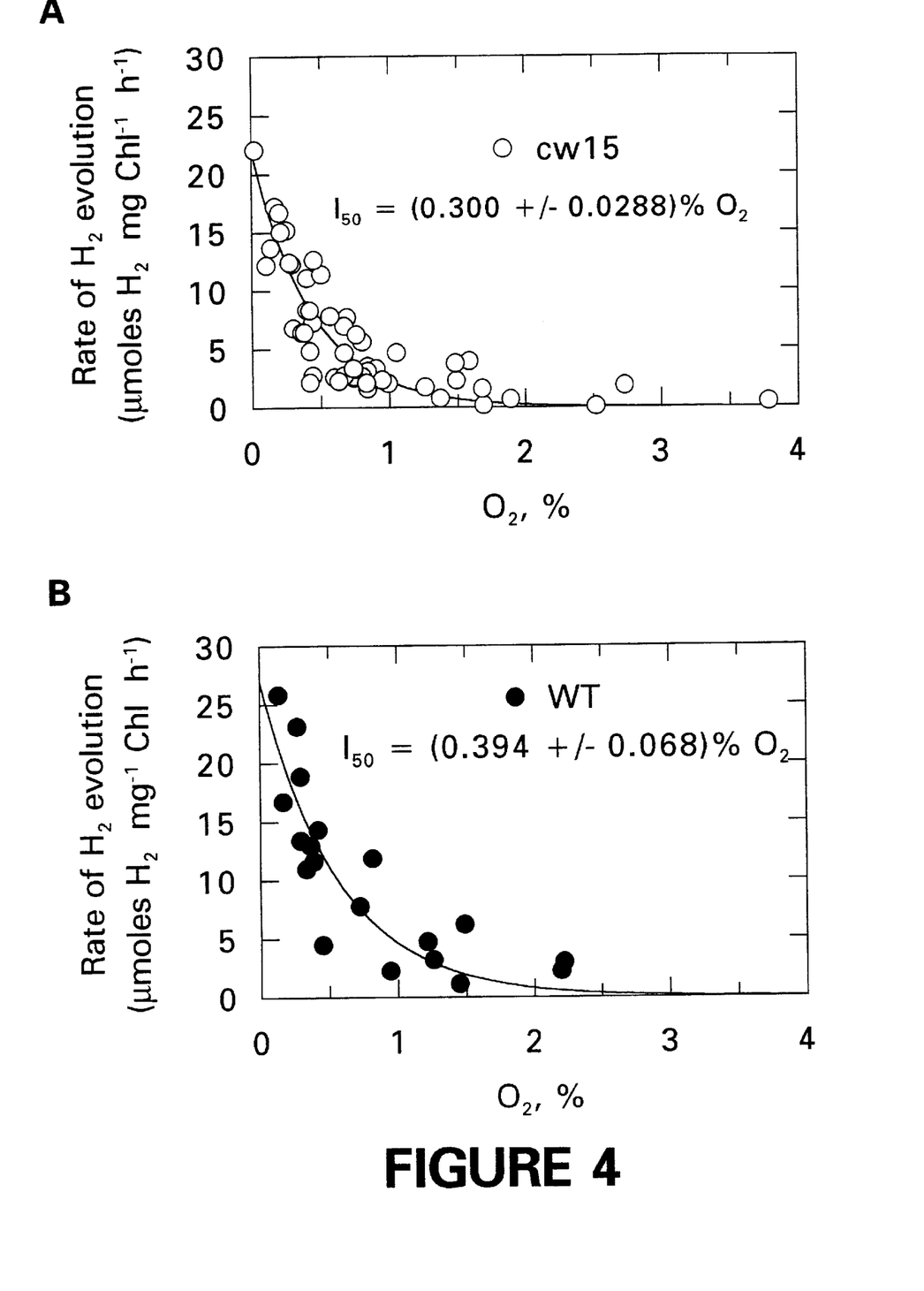
FIGS. 4A and 4B shows normalized rates of $H_2$ evolution measured with pre-induced (A) cw15 or (B) WT (wild-type) cells injected to an assay medium pre-set to the indicated initial concentrations of $O_2$. $H_2$ concentration in the assay medium was measured immediately, and the procedure included a 2-minute interval prior to illumination to allow the cells to acclimate. No $H_2$ production was observed during this 2-minute time, as hereinafter described in the Materials and Methods Section.

Confirmation of the validity of the techique or process to select for $O_2$-tolerant, $H_2$-producing organisms comes from measurement of the $O_2$-sensitivity of $H_2$-production of the surviving isolates from two different selection experiments, compared to their parental strains. To establish base line values, we initially determined the $O_2$ sensitivity of $H_2$ production by WT and cw15 cells. Initial rates of $H_2$ evolution were measured, as described in the Materials and Methods section, as a function of the initial concentrations of $O_2$ in the assay medium. Given the variability of measuring rates of $H_2$ evolution from day to day, the data from each experiment (from 5 to 10 points) were fitted to a single exponential decay equation from which we estimated $V_o$, the rate of $H_2$ evolution in the absence of $O_2$, and $I_{50}$, the initial $O_2$ concentration that causes a 50 percent decrease in the initial rate of $H_2$ evolution compared to $V_o$. The $V_o$s estimated from each experiment were then used to normalize the data obtained from all the experiments. The data in FIG. 4 show that as the initial concentration of $O_2$ increases, the rate of $H_2$ evolution by cw15 (FIG. 4A) or WT cells (FIG. 4B) decreases exponentially. The normalized $V_o$ values for the cw15 and WT strains in this series of experiments were respectively, 22 and 27 $\mu$moles $H_2 \cdot mg\ Chl^{-1} \cdot h^{-1}$, and the estimated $I_{50}$s were 0.300±0.28% and 0.394%±0.068% O2. Much higher $V_o$s (see FIG. 5) can be obtained with more active cells and better assay techniques.

Because of the variability in rates measured on different days, we always determined the $O_2$ sensitivity of $H_2$ production for survivors from different MNZ experiments and their respective parental strains on the same day. The results from two selection experiments are reported in Table I. Experiment I was done with pre-induced cw15 and WT cells treated with 58 mM MNZ in the presence of 2.8% $O_2$. There were six cw15 survivors, of which we tested two, and both showed increases in the $I_{50}$ for $O_2$ compared to their parental strains. One particular survivor, identified as D5, had an estimated $I_{50}$ 2.3 times higher than its parental strain. The other CW15 survivor, despite a higher $I_{50}$ had a decreased $V_o$ rate of $H_2$ evolution, which appeared to indicate lower rates of electron transport.

TABLE I

Results From Two $H_2$ Production Selection Experiments Done With cw15 and WT *Chlamydomonas reinhardtii* Cells*

| Experiment | Isolate (parental strain) | $I_{50}$ for $O_2$ (% of parental strain) | $V_o$ (% of parental strain) |
|---|---|---|---|
| Experiment I (2.8% $O_2$) | D5 (cw15) | 233 | 100 |
|  | D4 (cw15) | 153 | 20 |
|  | B1 (WT) | 152 | 100 |
|  | B2 (WT) | 163 | 12 |
| Experiment II (5% $O_2$) | A4 (WT) | 100 | 23 |
|  | A6 (WT) | 138 | 44 |
|  | A11 (WT) | 168 | 21 |
|  | A12 (WT) | 100 | 5 |

*The cells were pre-induced and subsequently treated with 58 mM MNZ for 20 minutes under 200 W/m² illumination in the presence of either %2.8 $O_2$ or 5% $O_2$. Survivors from the two experiments were plated, and selected clones were transferred to liquid medium and grown photoautotrophically for 3 days. Pre-induced cells were used in measurements of $H_2$-evolution rates in the presence of different initial $O_2$ concentrations as in FIG. 4. Estimated $V_o$ and $I_{50}$ values for $H_2$ production obtained for each survivor were compared to values determined with control parental WT and cw15 cells on tha same day.

MNZ treatment of WT cells in Experiment I yielded 5 survivors. Two of them showed increases in $I_{50}$ in the order of 50% compared to their parental strain. The rates of $H_2$ evolution by one of the survivors was very low, but the other had rates comparable to those of its parental strain. Experiment II was done only with WT cells following pre-induction of the hydrogenase and MNZ treatment in the presence of 5% $O_2$. All of the four tested survivors out of a total of six had lower rates of $H_2$ evolution. Two of them had $I_{50}$s in the order of their parental strain, while the other two exhibited small increases in their $I_{50}$ s.

The following variables during MNZ treatment were shown to affect the rate of cell survival: MNZ concentration, light intensity, pre-induction of the hydrogenase enzyme, and $O_2$ concentration. Both higher concentrations of MNZ and higher light intensities are more toxic to Chlamydomonas cells. The effect of higher light intensity appears due to increased electron transport to Fd. The response of treated cells to MNZ treatment is first order with respect to MNZ when non-induced cells are used. However, if the hydrogenase enzyme is pre-induced by anaerobic incubation before the selective treatment, the response is non-exponential. This suggests that the toxic effect of the drug is limited by the presence of an alternative electron transport pathway from Fd in these cells. Addition of oxygen during the selective treatment increases the toxicity of MNZ, due to inactivation of the hydrogenase enzyme; however, the effect (FIG. 3) is not very pronounced, apparently because it is superimposed on light-induced, internally-generated $O_2$.

After being assured that the toxicity of MNZ can be correlated with the activity of the hydrogenase in Chlamydomonas cells under these experimental conditions, we applied the selection to a population of wild-type cells, and tested some of the survivors for the sensitivity of their hydrogenases to added oxygen. Oxygen sensitivity was measured as a $H_2$ evolution $I_{50}$ for $O_2$, that is, the oxygen concentration that inhibits half of the initial rate of $H_2$ evolution measured in the absence of $O_2$. Again, Table I shows the results from the two experiments, done either at 2.8% or 5% $O_2$. Wild-type (WT) or cell wall-less (cw15) Chlamydomonas cells were used in these experiments.

It is clear that the treatment allows for the survival of two types of isolates: (a) those that have lower rates of $H_2$ evolution (apparently because of lower rates of electron transport to Fd due to defective electron transport carriers or antenna mutations) and unchanged sensitivity to $O_2$, and (b) those that have unchanged rates of $H_2$ evolution but higher tolerance to $O_2$.

The isolate D5 from Experiment I (Table I), which shows an $I_{50}$ for $O_2$ that is much higher than its parental strain, was first subjected to mutagenesis treatement and then submitted to the selection treatment under the more stringent condition (5% $O_2$). Table II shows the results from the experiment. Two out of seven tested survivors exhibit increases in $I_{50}$ for $O_2$. In the case of IM6 mutant, the increase in $I_{50}$ brings it up to 1.4% $O_2$, a value that is over 4 times higher than that of the initial cw15 strain (0.3% $O_2$).

TABLE II

Hydrogen Evolution Characteristics of Survivors from a $H_2$-Producing Selection Experiment Done in the Presence of 5% $O_2$

| Isolate* | $I_{50}$, % of parental strain (D5) | $V_o$ % of parental strain (D5) |
|---|---|---|
| IM1 | 82 | 160 |
| IM2 | 66 | 90 |
| IM3 | 108 | 61 |
| IM4 | 157 | 61 |
| IM5 | 86 | 39 |
| IM6 | 148 | 136 |
| IM7 | 151 | 44 |

*The parental strain for this experiment was the D5 variant isolated previously (see Table I). The IM6 survivor was the best isolated obtained from this selection experiment.

Figure 5:
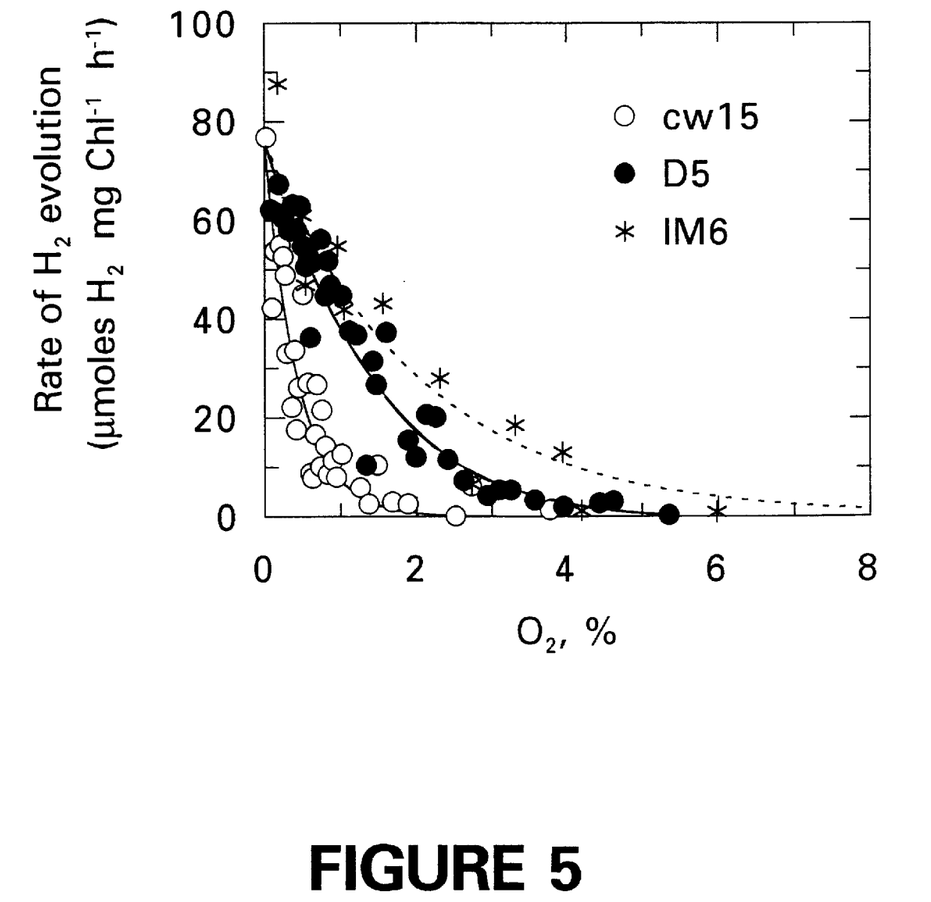

The gradual increase in $I_{50}$ obtained by two rounds of selective pressure can be seen in FIG. 5, which is a plot of the initial rate of $H_2$ evolution as a function of $O_2$ concentration in the assay medium. Initial rates of $H_2$ evolution were normalized to $V_o$ values observed for the D5 strain grown under optimal conditions. Open circles correspond to measurements done with the cell wall-less parental strain cw15; its $H_2$ evolution $I_{50}$ for $O_2$ was 0.3%. Closed circles represent the first variant, D5, obtained from the selective pressure applied in the presence of 2.8% $O_2$; its estimated $I_{50}$ was 1.0%. Asterisks correspond to measurements done with mutant IM6, obtained from the second round of selective pressure (in the presence of 5% $O_2$) applied to mutagenized D5 cells; its estimated $I_{50}$ was 1.4% (The relative $I_{50}$ values reported in Tables I and II represent estimates from a single experiment).

Although the examples have been conducted wth algae, it is to be understood that the selection technique of the invention also works with cyanobacteria of blue-green algae—and specifically with the genus Spirilina. Therefore, in the context of the invention, algal cells will include cyanobacteria (blue-green algae), and particularly those as the genus Spirilina.

While the foregoing examples have been written with respect to specific embodiments, the essence or spirit of the invention is not limited thereto and various modifications which would be obvious to one skilled in the art are intended to be encompassed herein.

We claim:

1. A process for selection of oxygen-tolerant, $H_2$-producing algal mutant cells comprising:

(a) growing algal cells photoautotrophically under fluorescent light to mid log phase;

(b) inducing algal cells grown photoautotrophically under fluorescent light to mid log phase in step (a) anaerobically by (1) resuspending the cells in a buffer solution at a range from about 6.8 to about 7.2 pH and making said suspension anaerobic with an inert gas; (2) incubating the suspension in the absence of light at ambient temperature;

(c) treating the cells from step (b) with metronidazole, sodium azide, and added oxygen to controlled concentrations in the presence of white light.

(d) washing off metronidazole and sodium azide to obtain final cell suspension;

(e) plating said final cell suspension on a minimal medium and incubating in light at a temperature sufficient to enable colonies to appear;

(f) counting the number of colonies to determine the percent of mutant survivors; and (g) testing survivors to identify oxygen-tolerant mutants that produce $H_2$ at high rates.

2. The process of claim 1, wherein, in step (b)(1) cells are *Chlamydomonas reinhartii* cells, said buffer is potassium phosphate and $MgCl_2$, and said inert gas is argon.

3. The process of claim 2, wherein, in step (c) said cells are treated with metronidazole, sodium azide, and oxygen for about 20 minutes; and in step (c) said incubating in light is done at about 24° C.

4. The process of claim 3, wherein in step (b) potassium phosphate is present in the amount of about 50 mM; said $MgCl_2$ is present in the amount of about 3.0 mM; and said pH is about 7.2.

5. The process of claim 4, wherein the amount of fluorescent light in step (a) is about 10 $W/m^2$.

6. The process of claim 5, wherein in step (b)(2) incubating said suspension in the absence of light at ambient temperature is for a period of from about 30 minutes to about 5 hours.

7. The process of claim 6, wherein in step (c) said treated stored cells are present in an amount of about $1.8 \times 10^5$ cells/ml.

8. The process of claim 7, wherein metronidazole is present in the amount of about 58 mM; sodium azide is present in the amount of about 1 mM; and white light intensity is about 200 $W/m^2$.

9. The process of claim 8, wherein in step (e) said temperature sufficient to enable colonies to appear is about 24° C.

10. The process of claim 1, wherein in step (a) said algal cells are grown photoautotrophically under fluorescent light to mid log phase at a temperature of about 24° C.

* * * * *